United States Patent
Miller et al.

(10) Patent No.: US 9,622,651 B2
(45) Date of Patent: Apr. 18, 2017

(54) WIRELESS LARYNGOSCOPE SIMULATOR WITH ONBOARD EVENT RECORDING ADAPTED FOR LARYNGOSCOPY TRAINING

(71) Applicant: Kb Port LLC, Allison Park, PA (US)

(72) Inventors: Charles G. Miller, Allison Park, PA (US); Clifford P Olmstead, Allison Park, PA (US)

(73) Assignee: KbPort LLC, Pittsburgh, PA (US)

( * ) Notice: Subject to any disclaimer, the term of this patent is extended or adjusted under 35 U.S.C. 154(b) by 481 days.

(21) Appl. No.: 13/750,156

(22) Filed: Jan. 25, 2013

(65) Prior Publication Data

US 2013/0197312 A1    Aug. 1, 2013

Related U.S. Application Data

(60) Provisional application No. 61/591,656, filed on Jan. 27, 2012.

(51) Int. Cl.
| | |
|---|---|
| *A61B 1/267* | (2006.01) |
| *A61B 1/06* | (2006.01) |
| *A61B 1/04* | (2006.01) |
| *A61B 1/00* | (2006.01) |
| *A61B 1/05* | (2006.01) |

(52) U.S. Cl.
CPC ............ *A61B 1/267* (2013.01); *A61B 1/0002* (2013.01); *A61B 1/00009* (2013.01); *A61B 1/00016* (2013.01); *A61B 1/00039* (2013.01); *A61B 1/00045* (2013.01); *A61B 1/04* (2013.01); *A61B 1/06* (2013.01); *A61B 1/00034* (2013.01); *A61B 1/05* (2013.01); *A61B 1/0676* (2013.01)

(58) Field of Classification Search
CPC .......... A61B 1/267; A61B 1/05; A61B 1/0676
USPC ................ 600/188, 190, 193, 197, 199, 185
See application file for complete search history.

(56) References Cited

U.S. PATENT DOCUMENTS

| | | |
|---|---|---|
| 2,769,441 A | 11/1956 | Abramson |
| 2,800,344 A | 7/1957 | Wolcott |
| 3,595,222 A | 7/1971 | Vellacott et al. |
| 3,766,909 A | 10/1973 | Ozbey |
| 3,884,222 A | 5/1975 | Moore |
| 3,900,021 A | 8/1975 | Makepeace et al. |
| 3,943,920 A | 3/1976 | Kandel |
| 4,086,919 A | 5/1978 | Bullard |

(Continued)

*Primary Examiner* — David Bates
*Assistant Examiner* — Olivia C Chang
(74) *Attorney, Agent, or Firm* — Buchanan Ingersoll & Rooney PC

(57) ABSTRACT

A laryngoscope has a first and second handle portion defining an internal cavity and forming a handle assembly. The laryngoscope includes a first and second blade portion defining an internal cavity and forming a blade assembly. A light and camera source within the internal cavity of the blade assembly illuminates at least a portion of the blade assembly and obtains images of the operation of the laryngoscope. A microprocessor coupled to the camera is mounted within one internal cavity and can record images from the camera. The microprocessor provides on-board recording capable of capturing video and audio and event data, such as from a simulator. A keypad is configured to provide for on-Board event flagging of the recorded data recorded by the microprocessor. The microprocessor may wirelessly transmit data from the laryngoscope.

16 Claims, 2 Drawing Sheets

(56) References Cited

U.S. PATENT DOCUMENTS

| | | |
|---|---|---|
| 4,126,127 A | 11/1978 | May |
| 4,273,112 A | 6/1981 | Heine et al. |
| 4,294,235 A | 10/1981 | Storz |
| 4,295,465 A | 10/1981 | Racz et al. |
| 4,305,386 A | 12/1981 | Tawara |
| 4,306,547 A | 12/1981 | Lowell |
| 4,323,304 A | 4/1982 | Ishii |
| 4,337,761 A | 7/1982 | Upsher |
| 4,360,008 A | 11/1982 | Corazzelli, Jr. |
| 4,406,280 A | 9/1983 | Upsher |
| 4,413,278 A | 11/1983 | Feinbloom |
| 4,437,458 A | 3/1984 | Upsher |
| 4,484,896 A | 11/1984 | Kohnke |
| 4,491,865 A | 1/1985 | Danna et al. |
| 4,527,553 A | 7/1985 | Upsher |
| 4,546,762 A | 10/1985 | Upsher |
| 4,557,256 A | 12/1985 | Bauman |
| 4,565,187 A | 1/1986 | Soloway |
| 4,573,451 A | 3/1986 | Bauman |
| 4,575,784 A | 3/1986 | Diau |
| 4,592,343 A | 6/1986 | Upsher |
| 4,651,202 A | 3/1987 | Arakawa |
| 4,736,734 A | 4/1988 | Matsuura et al. |
| 4,807,594 A | 2/1989 | Chatenever |
| 4,815,451 A | 3/1989 | Bauman |
| 4,844,071 A | 7/1989 | Chen et al. |
| 4,877,016 A | 10/1989 | Kantor et al. |
| 4,878,485 A | 11/1989 | Adair |
| 4,901,708 A | 2/1990 | Lee |
| 4,905,669 A | 3/1990 | Bullard et al. |
| 4,918,521 A | 4/1990 | Yabe et al. |
| 4,924,855 A | 5/1990 | Salerno et al. |
| 4,947,896 A | 8/1990 | Bartlett |
| 4,958,624 A | 9/1990 | Stone et al. |
| 4,982,729 A | 1/1991 | Wu |
| 4,989,586 A | 2/1991 | Furukawa |
| 5,003,963 A | 4/1991 | Bullard et al. |
| 5,101,807 A | 4/1992 | Kawashima |
| 5,178,132 A | 1/1993 | Mahefky |
| 5,183,031 A | 2/1993 | Rossoff |
| 5,203,320 A | 4/1993 | Augustine |
| 5,263,472 A | 11/1993 | Ough |
| 5,279,281 A | 1/1994 | Harvey |
| 5,349,943 A | 9/1994 | Ruiz |
| 5,355,870 A | 10/1994 | Lacy |
| 5,363,838 A | 11/1994 | George |
| 5,363,839 A | 11/1994 | Lankford |
| 5,363,840 A | 11/1994 | Silva |
| 5,381,787 A | 1/1995 | Bullard |
| 5,408,992 A | 4/1995 | Hamlin et al. |
| 5,425,356 A | 6/1995 | Ough |
| 5,443,058 A | 8/1995 | Ough |
| 5,494,483 A | 2/1996 | Adair |
| 5,498,231 A | 3/1996 | Franicevic |
| 5,527,261 A | 6/1996 | Monroe et al. |
| 5,529,570 A | 6/1996 | Storz |
| 5,591,119 A | 1/1997 | Adair |
| 5,603,688 A | 2/1997 | Upsher |
| 5,630,783 A | 5/1997 | Steinberg |
| 5,643,221 A | 7/1997 | Bullard |
| 5,651,761 A | 7/1997 | Upsher |
| 5,701,904 A | 12/1997 | Simmons et al. |
| 5,702,351 A | 12/1997 | Bar-Or et al. |
| 5,776,052 A | 7/1998 | Callahan |
| 5,800,344 A | 9/1998 | Wood et al. |
| 5,819,727 A | 10/1998 | Linder |
| 5,827,178 A | 10/1998 | Berall |
| 5,845,634 A | 12/1998 | Parker |
| 5,846,183 A | 12/1998 | Chilcoat |
| 5,846,186 A | 12/1998 | Upsher |
| 5,873,818 A | 2/1999 | Rothfels |
| 5,879,289 A * | 3/1999 | Yarush et al. ............... 600/179 |
| 5,879,304 A | 3/1999 | Shuchman et al. |
| 5,888,193 A | 3/1999 | Breidenthal et al. |
| 5,897,489 A | 4/1999 | Urbanowicz et al. |
| 5,897,491 A | 4/1999 | Kastenbauer et al. |
| 5,906,576 A | 5/1999 | Upsher |
| 5,913,816 A | 6/1999 | Sanders et al. |
| 5,921,917 A | 7/1999 | Barthel et al. |
| 5,941,816 A | 8/1999 | Barthel et al. |
| 5,951,461 A | 9/1999 | Nyo et al. |
| 5,954,632 A | 9/1999 | Heckele et al. |
| 5,973,728 A | 10/1999 | Levitan |
| 5,993,383 A | 11/1999 | Haase |
| 6,004,263 A | 12/1999 | Nakaichi et al. |
| 6,013,026 A | 1/2000 | Krauter et al. |
| 6,036,639 A | 3/2000 | Allred, III et al. |
| 6,083,151 A | 7/2000 | Renner et al. |
| 6,090,040 A | 7/2000 | Metro |
| 6,095,972 A | 8/2000 | Sakamoto |
| 6,123,666 A | 9/2000 | Wrenn et al. |
| 6,135,948 A | 10/2000 | Lee |
| 6,139,491 A | 10/2000 | Heine et al. |
| 6,146,402 A | 11/2000 | Munoz |
| 6,186,944 B1 | 2/2001 | Tsai |
| 6,217,514 B1 | 4/2001 | Gruen et al. |
| 6,248,061 B1 | 6/2001 | Cook, Jr. |
| 6,251,069 B1 | 6/2001 | Mentzelopoulos et al. |
| 6,277,068 B1 | 8/2001 | Wojnowicz et al. |
| 6,350,235 B1 | 2/2002 | Cohen et al. |
| 6,354,993 B1 | 3/2002 | Kaplan et al. |
| 6,652,453 B2 | 11/2003 | Smith et al. |
| 6,840,903 B2 | 1/2005 | Mazzei et al. |
| 6,890,298 B2 | 5/2005 | Berci et al. |
| 7,156,091 B2 | 1/2007 | Koyama et al. |
| 7,988,622 B2 * | 8/2011 | Achas Gandarias ......... 600/188 |
| 2001/0014768 A1 | 8/2001 | Kaplan et al. |
| 2003/0195390 A1 | 10/2003 | Graumann |
| 2005/0054903 A1 | 3/2005 | Cantrell |
| 2007/0179342 A1 | 8/2007 | Miller et al. |
| 2009/0247833 A1 * | 10/2009 | Tanaka ........................ 600/188 |
| 2012/0078055 A1 * | 3/2012 | Berci ................ A61B 1/0005 600/188 |
| 2013/0066153 A1 * | 3/2013 | McGrath ........... A61B 1/00034 600/188 |

\* cited by examiner

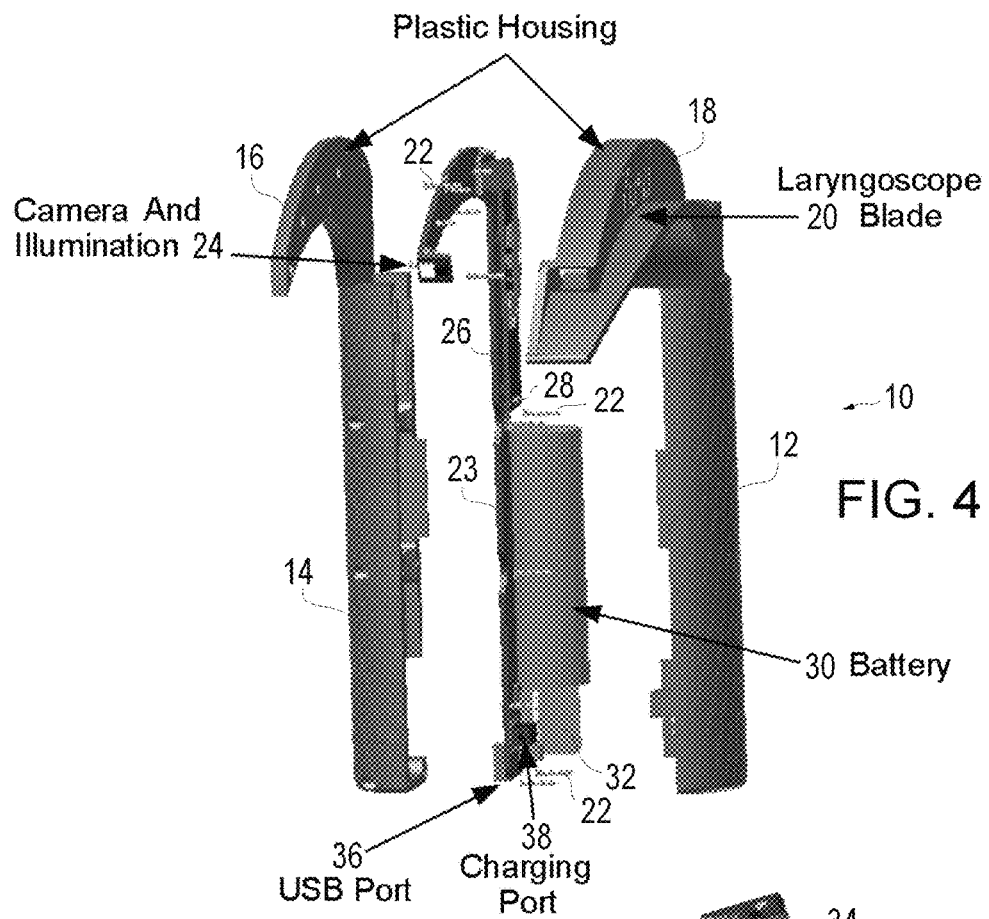
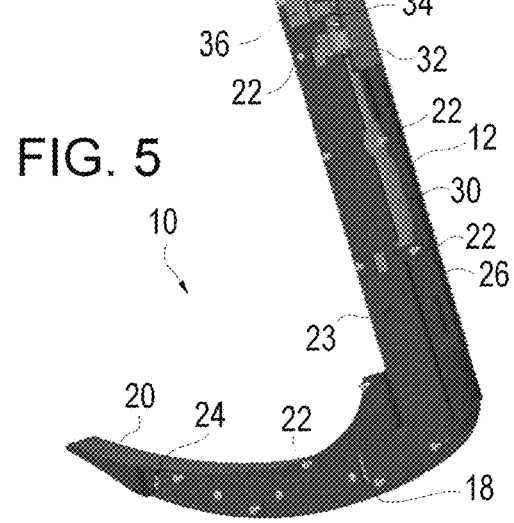

WIRELESS LARYNGOSCOPE SIMULATOR WITH ONBOARD EVENT RECORDING ADAPTED FOR LARYNGOSCOPY TRAINING

RELATED APPLICATIONS

This application claims the benefit of U.S. Provisional patent application Ser. No. 61/591,656 filed Jan. 27, 2012 entitled "Wireless Laryngoscope Simulator with Onboard Event Recording Adapted for Laryngoscopy Training."

BACKGROUND OF THE INVENTION

1. Field of the Invention

The present invention relates to a wireless laryngoscope and camera system, and more particularly to a wireless laryngoscope with onboard recording that is particularly well suited for laryngoscopy training.

2. Background Information

Dr. Richard M. Cooper of the Department of Anesthesia and Pain Management, Toronto General Hospital, University of Toronto has eloquently introduced the need and purpose for laryngoscope noting that "man's assumption of an upright posture, coupled with our tendency to live in social groups has resulted in some bad habits—simultaneous eating and talking. This has necessitated exclusion of the larynx from the line of sight connecting the mouth to the esophagus. While this does make eating safer and more interesting, it has complicated the task for airway managers."

Brief History of Laryngology

The early need for laryngeal visualization was noted by medical student Benjamin Guy Babington who created a "glottiscope" in 1829. A two pronged tool, one prong (or shank) depressed the tongue while the other was positioned along the palate, reflecting sunlight for illumination of the glottis. This device was later termed a laryngoscope by his contemporaries. In 1844, John Avery, a surgeon at London's Charing Cross Hospital developed a head-mounted mirror that reflected candlelight onto a mirror housed within a speculum. Manual Garcia (1805-1906), a professor of singing at the Royal Academy of Music in London is generally credited with the discovery of laryngoscopy. In 1854, while strolling in Paris, he saw the sun's image reflected in a store windowpane. He purchased a dental mirror for six francs and used this, in combination with a hand-held mirror reflecting sunlight, to visualize his own larynx and trachea during inspiration and vocalization. His discovery, which he termed "autolaryngoscopy" was presented to the Royal Society in May 1855 and at the age of 100, in 1905 he was honored by the most prominent laryngologists of his time as the Father of laryngology.

Ludwig Türck, a Viennese neurologist used a technique similar to Garcia's, though apparently unaware of the singing teacher's activities. He used self-made mirrors and performed laryngoscopy on his gagging patients until the autumn sun's diminished intensity forced him to abandon his efforts. Johann Czermak, a physician and physiologist from Budapest, using a table lamp and mirrors borrowed from Türck, performed laryngoscopy. Czermak published and demonstrated his findings widely. He initially acknowledged Türck's contribution, but subsequently withdrew this. What followed was a protracted public debate, referred to as the "Türckish war" about who actually first used laryngoscopy for diagnostic purposes.

A laryngology clinic was established in Vienna in 1870 and minor surgical procedures were performed under visual control. In the days prior to local anesthetics, patients had to be trained to suppress their gag reflexes. Morell Mackenzie learned laryngoscopy from Czermak and went on to found London's first throat hospital.

William Macewen, a British surgeon, was the first to intubate the larynx for surgical purposes. He practiced blind, digital intubation on cadavers and eventually employed this technique to perform a composite resection in 1878. Joseph O'Dwyer developed instruments to enable tracheal intubation which saved the lives of hundreds of children suffocating from diphtheria. Hans Kuhn modified O'Dwyer's instruments and created a long, flexible metal endotracheal tube and introducer but the technique still depended upon blind insertion, largely because light sources were inadequate to permit progress in direct laryngoscopy.

In 1895, Alfred Kirstein learned of an inadvertent tracheal insertion of an esophagoscope, and proceeded to develop a rigid laryngoscope with transmitted light. This consisted of a lamp within the handle, focused on a lens and redirected through the laryngoscope by a prism. Chevalier Jackson subsequently modified Kirstein's laryngoscope by providing distal illumination with a tungsten bulb. In 1913, Henry Janeway devised an open-sided laryngoscope with battery operated distal illumination, specifically for endotracheal intubation.

In 1941, Robert Miller introduced a new, longer, lower profile laryngoscope blade (a straighter blade), designed to pick up the epiglottis. This blade required limited mouth opening but also left little space to manipulate the endotracheal tube (ETT). Two years later, Robert Macintosh described a curved blade, designed to elevate the epiglottis by exerting its force on the base of the tongue. He believed that reducing contact with the epiglottis would be less stimulating and provide more room for manipulation of the ETT. These two blade designs, known as the "Miller blade" and the "Mac blade" or "Macintosh Blade" were quickly and widely adopted.

Modern Laryngoscopy

The "Miller blade" and the "Mac blade" or "Macintosh Blade" both continue to dominate the field of laryngoscopy and these blade forms represent more than 95% of the laryngoscopic blades used in practice. The proper function of both a Macintosh and Miller blade is dependent on using an appropriate length of blade. The Macintosh blade must be long enough to put tension on the glossoepiglottic ligament, and the Miller blade must be long enough to trap the epiglottis against the tongue. Both blade types are made in various designated sizes (but the overall distinctive shape is as described above). Thus, in some patients, it may be appropriate to change the length of the conventional Mac or Miller blade in order to obtain proper blade function. The changing of the length can be through replaceable blades that is common in laryngoscopes or through selecting a separate laryngoscope altogether.

In some patients, a Macintosh blade may provide a superior view or intubating conditions than a Miller blade, and vice versa. A Macintosh blade is generally regarded as a better blade whenever there is little upper airway room to pass the ET (e.g., small narrow mouth, palate, oropharynx), and a Miller blade is generally regarded as a better blade in patients who have a small mandibular space (anterior larynx), large incisors, or a long, floppy epiglottis. Although the skill that the practitioner has with each style may also be determinative of which design is best suited for particular applications.

A study that examined airway problems in over 18,500 adult non-obstetrical patients, direct larynoscopy was the first choice 98% of the time. Among these patients, the failure rate was 0.3% and "awkward" or "difficult" in 2.5% and 1.8% respectively. The study recognized that difficulties involving laryngoscopy and intubation are poorly described and proposed an intubation "difficulty score". No difficulties were encountered in 55% of adult patients; minor intubations difficulties were encountered in 37%; two or three laryngoscopies were required in 9% of cases and more than three attempts were required 3% of the time. However, even "non-difficult" endotracheal intubation may be associated with airway injury. One analysis involving 266 incidents of airway injury found that 80% of laryngeal injuries occurred when laryngoscopy and intubation was thought to have been easy.

The inability to properly visualize the larynx generally results in multiple or prolonged laryngoscopic attempts with increasing force, and is associated with esophageal, pharyngeal and dental injury, arterial desaturation, hemodynamic instability and unplanned intensive care unit admissions.

More recently, compact, robust, high-resolution videochips have become available which can be embedded within laryngoscopes. These devices provide an alternative laryngeal view. These devices permit simultaneous viewing by mentor and supervisor and have been thought to accelerate the instruction of laryngoscopy. These images can be captured and replayed for analysis to further expedite and improve training. The video or static images may be useful for research, teaching or clinical documentation. Also, these devices can enable visualization in settings that would otherwise be challenging or not possible. Additionally, it has been asserted that since tissues do not have to be compressed and distracted to achieve a line-of-sight, there may be less stress and trauma to the patient during laryngoscopy; and further that, positioning should not impact upon the laryngeal view.

Several different laryngoscopes with associated camera systems have been commercialized to some degree or another, with each system allowing for indirect viewing of obstructed airways. All of these systems rely on standard wired camera technologies to provide the intubator and other medical personnel with an indirect visualization of the field on view. The digital images from these commercial camera systems are transmitted via cable to an external monitor.

The inherent weaknesses of the systems using external viewing displays are that the cables connecting the camera, to the display, limits the movement of the intubator, which may complicate an already difficult procedure. An attached cable limits the working space for medical personnel and can also cause another potential hazard. Also, having exposed cabling leaves the system susceptible to fluids damaging the sensitive electronic systems no matter how well sealed. Furthermore, cables are easily damaged from over extension, frequent use, and any number of other factors adding a substantial point of failure to the entire system.

Wireless transmitters for such systems have been proposed that could, in theory, alleviate the problems encountered with cabled camera systems. See for example U.S. Patent Application Publication 2003/0195390 and U.S. Pat. No. 6,840,903, which are incorporated herein by reference. In both these systems the cable is replaced with an external antennae attached to a transmitter. The external antennae in each of these proposed wireless systems add a separate obstruction on the laryngoscope for the user. Further, as noted above, a significant advantage for the use of camera systems in laryngoscopes is for teaching and training purposes. Both of these prior art camera systems are directed to "specialized" blade shapes (non Miller or Mac styles), and promote the advantages of such unique blades.

The inventors of the present invention believe that training on "specialized" blades is not useful and possibly counter productive. Having trainees gain proficiency on a blade design they are not likely to see in the actual use is less desirable (and possibly counter productive) than having them gain proficiency on conventional blade designs. Within the meaning of this application the Mac blades (AKA Macintosh blades) and the Miller blades, as known in the art, are "conventional" blade designs for laryngoscopes.

Other prior art laryngoscopy related developments can be found in U.S. Pat. No. 6,652,453 disclosing a portable video laryngoscope; U.S. Pat. No. 6,840,903 by Nuvista Technology Company disclosing a laryngoscope with image sensor; U.S. Pat. No. 6,890,298 by Karl Storz GmbH & Co disclosing a video laryngoscope with a detachable light and image guide; and U.S. Patent Publication No. 2003/0195390 disclosing a digital laryngoscope with image sensor. These patents and published patent application are incorporated herein by reference.

Some of the inventors of the present application were also inventors of a prior laryngoscopy training aid disclosed in U.S. Patent 2007-0179342 which is incorporated herein by reference. As discussed in detail in the following application, the present invention includes substantially all of the advantages of the laryngoscopy training aid disclosed in U.S. Patent 2007-0179342 including the provision of (a) a wireless laryngoscope for remote viewing and capable of serving as an intubation instrument, for standard intubations and complicated intubations where the field of view is obstructed from the intubator and/or other medical staff; (b) a laryngoscope, which is similar in design and functionality to existing blade and handle shapes so that the intubator is familiar with its application, and such that the laryngoscope is particularly well suited for training applications; and (c) an electronic laryngoscope with a self-contained wireless digital camera embedded within the laryngoscope, which provides real-time indirect viewing of the field of view that is also self-contained, light weight, and portable, and wherein this image may selectively be transmitted wirelessly to a remote receiver and can be viewed on any video type display.

The prior laryngoscopy training aid disclosed and described in U.S. Patent 2007-0179342 however fails to provide on-board recording capable of capturing audio, video, and/or event data, or on-Board event flagging. It is an object of the present invention to maintain substantially all of the advantages of the prior laryngoscopy training aid disclosed in U.S. Patent 2007-0179342 and address the deficiencies of this prior art system.

SUMMARY OF THE INVENTION

The present invention provides a wireless laryngoscope for remote viewing and capable of serving as an intubation instrument, for standard intubations and complicated intubations where the field of view is obstructed from the intubator and/or other medical staff and which is configured for provide on-board recording capable of capturing audio, video, and/or event data, including data from associated simulators.

Further the present invention provides a laryngoscope, which is similar in design and functionality to existing blade and handle shapes so that the intubator is familiar with its application, and such that the laryngoscope is particularly well suited for training applications and wherein the laryngoscope includes onboard event flagging capabilities.

The present invention further provides an electronic laryngoscope with a self-contained wireless digital camera embedded within the laryngoscope, which provides real-time indirect viewing of the field of view that is also self-contained, light weight, and portable. This image can be recorded onboard, transmitted wirelessly real time to its receiver and can be viewed on any video type display, or transferred latter for subsequent viewing, or any combination thereof.

The present invention further provides an electronic laryngoscope with On-Board event flagging, such as via a keypad. The present invention further provides an electronic laryngoscope with Adjustable LED illumination and with USB connection for transferring recorded data for debriefing or archiving. The present invention further provides an electronic laryngoscope with an operator controlled keypad for on/off control of the device, operator controlled record/stop/transmit control of the device, onboard operator controlled flagging, and operator controlled lighting intensity functionality.

This invention is intended such that as trainees or users gain proficiency with the present invention it will directly translate to proficiency with conventional non-camera based laryngoscopes.

One embodiment of the present invention provides a wireless laryngoscope having a first handle portion and a second handle portion coupled to the first handle portion and defining an internal cavity, wherein the first handle and the second handle portions combine to form a handle assembly. The laryngoscope further includes a first blade portion and a second blade portion coupled to the first blade portion and defining an internal cavity in at least a portion thereof, wherein the first blade portion and the second blade portion combine to form a blade assembly. A light source and camera are mounted within the internal cavity of the blade assembly for illuminating at least a portion of the blade assembly and for obtaining images of the operation of the laryngoscope. An onboard microprocessor is coupled to the camera and is mounted within one internal cavity and is configured to selectively record and/or wirelessly transmits the video images of the camera to a remote receiver.

In one aspect of the invention the first blade portion is formed integral with the first handle portion and the second blade portion is formed integral with the second handle portion. In one aspect of the invention the blade assembly is one of a Miller blade and a Macintosh blade.

In one aspect of the invention a method of training laryngoscopy is provided comprising the steps of: providing a wireless training laryngoscope; and recording onboard the laryngoscope trainee intubation attempts using the training laryngoscope. The method may further provide that at least some of the intubation attempts using the training laryngoscope are performed on simulators and that data from the simulator is recorded onboard the laryngoscope.

These and other advantages of the present invention will be clarified in the brief description of the preferred embodiment taken together with the drawings in which like reference numerals represent like elements throughout.

BRIEF DESCRIPTION OF THE DRAWINGS

FIG. 4 is an exploded front perspective view of the wireless laryngoscope of FIG. 1; and FIG. 5 is side perspective view of the wireless laryngoscope of FIG. 1 with one housing portion removed for clarity.

DESCRIPTION OF THE PREFERRED EMBODIMENTS

Figure 1:
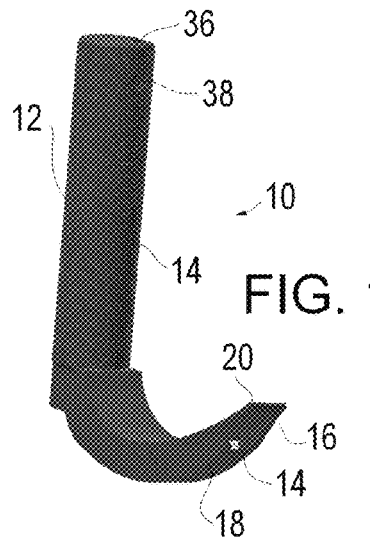
FIG. 1 is a front perspective view of a wireless laryngoscope with onboard recording that is particularly well suited for laryngoscopy training in accordance with one aspect of the present invention.
Figure 2:
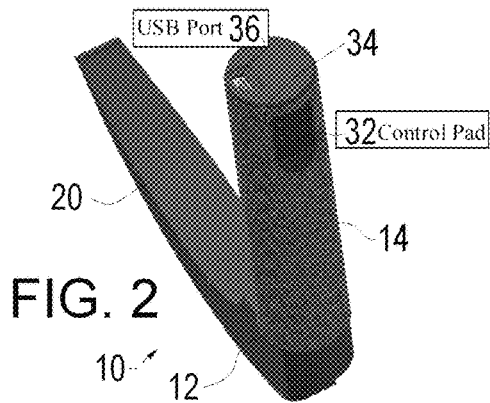
FIG. 2 is a top rear perspective view of the wireless laryngoscope of FIG. 1.
Figure 3:
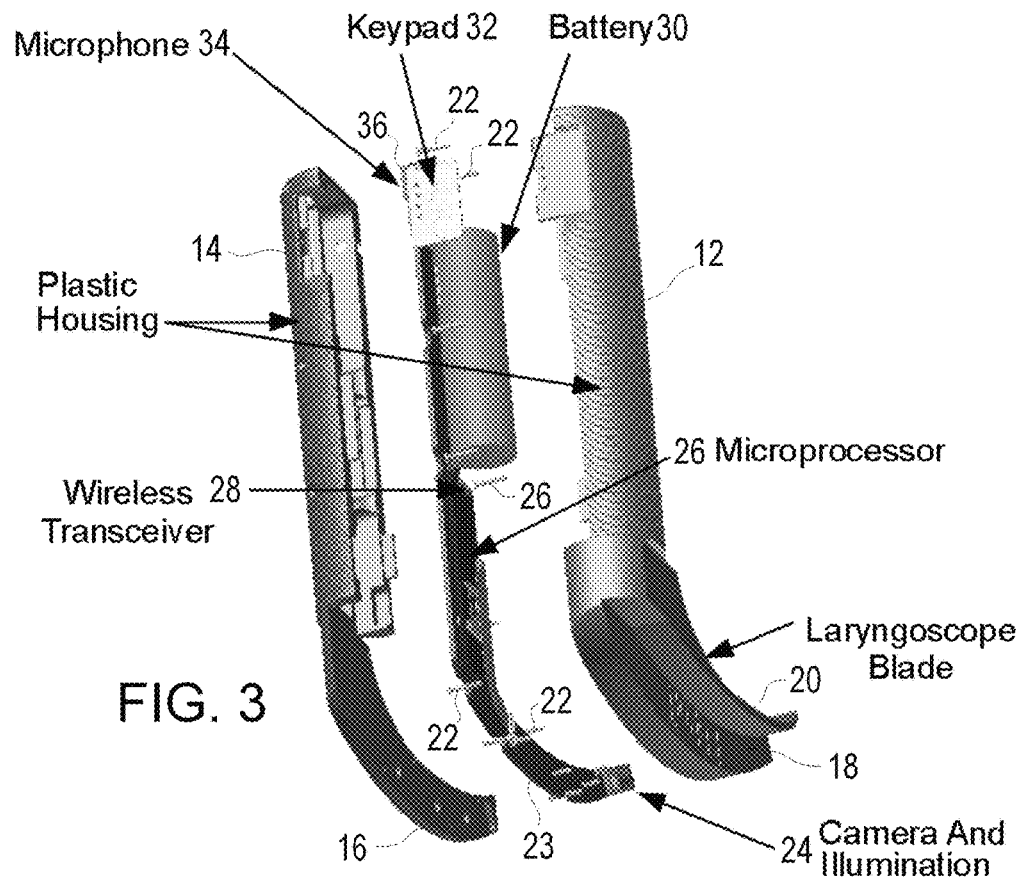
FIG. 3 is an exploded rear perspective view of the wireless laryngoscope of FIG. 1.

FIG. 1 is a front perspective view of a laryngoscope 10 according to the present invention. The laryngoscope 10 includes a front or first handle portion 12 and a second or rear handle portion 14 coupled to the first handle portion 12 and defining an internal cavity as described below. The first handle and the second handle portions 12 and 14 combine to form a handle assembly which is intended to conform to the general size and shape of conventional laryngoscope designs. The terms front and rear are merely to differentiate the handle portions 12 and 14 for purposes of explanation only. The handle portions 12 and 14 are made from any conventional material, although injection molded thermoplastic is cost effective, particularly for training purposes. In training purposes the laryngoscope 10 will likely be used on simulators (not shown) such that the laryngoscope need not be sterilized (autoclaving or the like) between uses. Consequently for constructing a training laryngoscope 10 for use with simulators a wider range of acceptable materials may be utilized.

The laryngoscope 10 further includes a front or first blade portion 18 and a rear or second blade portion 16 coupled to the first blade portion 18 and defining an internal cavity in at least a portion thereof as described below. The first blade portion 18 generally forms a blade assembly including a conventional extension or tongue 20, although the second blade portion as shown can be consider to combine with the first blade portion 18 to form this structure as illustrated.

It is important for training purposes that the blade assembly of the present invention be formed in a conventional blade shape, specifically one of a Miller blade and a Macintosh blade. As shown the blade assembly is a Macintosh blade, specifically a "Mac 3" as shown. The Mac blades and the Miller blades are consider the conventional blade designs within this application. The conventional blade design is preferred even if the associated camera system allows, or even suggests as some have postulated, for an alternative blade configuration. For training purposes it is desired that the intubators gain proficiency with a style that they will likely utilize in the field (and which is likely NOT to have camera system associated therewith).

The laryngoscope 10 still provides all the advantages of a camera laryngoscope discussed above and can easily be utilized in clinical application, but the laryngoscope 10 has particular training advantages as described herein.

The blade portions 16 and 18 are made from any conventional material, although injection molded thermoplastic is cost effective, particularly for training purposes. Further as illustrated in the figures, it is possible to easily construct the front handle portion 12 and the front blade portion 18 as an integral molded unit and the rear handle portion 14 and the rear blade portion 16 as integral molded units. The present invention provides a final "one-piece" laryngoscope 10 because the handle assembly is integral (not separable from) the blade assembly. Additionally as shown attaching the housing assembly and blade assembly components together can utilize a series of mechanical fasteners such as screws 22. Other conventional attaching members could also be used.

As a note separable or replaceable blade assembly would be considered a two piece construction within the meaning of this application. The "one piece" construction is believed to allow for easier construction of the internal components for the system.

A camera and LED light source 24 are mounted within an internal cavity of the blade assembly on an inner component board 23. The LED elements of the source 24 will provide illumination in a conventional fashion. The camera of the source 24 is for obtaining images of the operation of the laryngoscope and is directed generally toward the tongue 20 as shown. The LED lighting elements of source 24 is preferably adjustable to allow for user adjustment of the desired amount of light during use.

An onboard microprocessor 26 is attached to board 23 and is coupled to the camera and light source 24. The microprocessor is positioned within one internal cavity and is configured to selectively record video images of the camera and/or wirelessly transmits the video images of the camera to a remote receiver (not shown). The microprocessor includes a wireless transceiver component for selectively transmitting the video images. The microprocessor 26 provides on-board recording capable of capturing and or transmitting video via camera from source 24 and audio from a microphone 34 coupled thereto. Further the microprocessor 26 provides on-board recording capable of capturing and or transmitting event data.

One type of event data stored by the microprocessor 26 may include event flagging and wherein the laryngoscope 10 further includes a keypad 32 mounted on the board 23 and coupled to the microprocessor 26 and configured to provide for on-Board event flagging via the keypad 32 of the recorded data recorded by the microprocessor 26.

Another type of event data stored by the microprocessor 26 may come from a simulator (not shown) and be sent to the microprocessor 26 via the transceiver 28. For example a medical patient simulator can transmit the simulators patient parameters to the microprocessor during a recorded training event.

Another type of event data stored by the microprocessor 26 sent to the microprocessor 26 via the transceiver 28 may be event flags such as may be submitted by a training supervisor during a training event. Other types of event data stored by the microprocessor 26 sent to the microprocessor 26 via the transceiver 28 could possibly include external video and or audio inputs of the recorded training event. The operational formatting of the microprocessor 26 can be found in greater detail in applicant's prior U.S. Patent Publication 2008/01224694, in the description of the controller therein, and this publication is incorporated herein by reference. Further this publication gives a further list of the types of inputs that can be introduced as event data. Additionally the microprocessor 26 of the present invention can be considered as an on-board operational equivalent of the ETC PRO+™ brand recording system sold by the applicants KB Port, Inc.

The transceiver 28 allows the selective transmission of the audio and video signals to an external recording system in the fashion of a wireless laryngoscope. The external recording system is preferably a system such as the ETC PRO+™ brand recording system sold by the applicants KB Port, Inc. The transceiver 28 allows the selective transmission of any collected event data as well.

The power supply is a rechargeable battery 30 mounted on board 23 received within the cavity of the laryngoscope 10 and which can be recharged through charging port 38 as generally known in the art. A USB port 36 is provided and coupled to the microprocessor to allow downloads to or from the microprocessor via a hardwired connection. The operator controlled keypad 32 provides for numerous user controls including for on/off control of the laryngoscope 10, operator controlled record/stop/transmit control of the laryngoscope 10, onboard operator controlled flagging, and operator controlled lighting intensity functionality for the light of source 24.

The laryngoscope 10 of the present invention provides a wireless laryngoscope 10 with onboard recording and transmitting capabilities that has conventional shape for the blade and the housing. All of this makes this laryngoscope 10 well suited for training purposes. Gaining proficiency on this laryngoscope 10 will allow the intubator trainee to gain proficiency on those laryngoscopes the trainee is likely to encounter in practice (i.e. the conventional laryngoscopes with Miller or Mac blades). Further the laryngoscope 10 facilitates training by allowing mentors to view (real time or via recording) the training attempts and to input event flags as needed both in real time or in post session reviews. The recording of intubation attempts will allow further review and comment to facilitate learning by the intubator and others. The laryngoscope 10 is not limited to training applications as it has all the advantages of a camera system laryngoscope with the additional advantages of a wireless implementation (and non-restricting internal antenna) as well as onboard recording.

The laryngoscope 10 is an affordable video laryngoscope easily designed to run the popular ETC™ brand recording software designed to help assist instructors in teaching students how to properly intubate a patient. The laryngoscope 10 may be effectively used in conjunction with medical simulators for efficient and effective training purposes. The all-in-one rigid laryngoscope 10, as shown, utilizes the popular "MAC3" blade design with an integrated camera and light source 24. Other blade designs are possible with the present invention. The laryngoscope 10 has the ability to record on-board or to selectively transmit the live audio, video, and data directly to a Windows installed client computer, to an ETC Pro+™ recording system, or similar system viewed as an auxiliary input. The laryngoscope 10 can allow Live Wireless viewing via Internet Explorer, and for Remote event flagging via Windows Explorer.

Although the present invention has been described with particularity herein, the scope of the present invention is not limited to the specific embodiment disclosed. It will be apparent to those of ordinary skill in the art that various modifications may be made to the present invention without departing from the spirit and scope thereof.

What is claimed is:

1. A laryngoscope simulator for training events comprising:
   a first handle portion;
   a second handle portion coupled to the first handle portion, together defining a handle internal cavity, wherein the first handle and the second handle portions combine to form a handle assembly at a proximal end of the laryngoscope;
   a first blade portion, wherein the first blade portion is formed integral with the first handle portion;
   a second blade portion coupled to the first blade portion, together defining a blade internal cavity in at least a portion thereof, wherein the first blade portion and the second blade portion combine to form a blade assembly at a distal end of the laryngoscope, wherein the second blade portion is formed integral with the second handle portion;

an integrated camera and light source within the internal cavity of the blade assembly for illuminating at least a portion of the blade assembly and for obtaining images of the operation of the laryngoscope;

a microprocessor coupled to the camera, said microprocessor mounted within one of the handle internal cavity and the blade internal cavity, wherein the microprocessor can record images from the camera and further receive and store event data, the event data comprising simulator data, external audio inputs, and external video inputs; and a keypad to provide on-board event flagging via the keypad of the recorded data recorded by the microprocessor.

2. The laryngoscope simulator for training events of claim 1 further comprising a transceiver to send and receive event flags remotely.

3. The laryngoscope simulator for training events of claim 2 wherein the blade assembly is one of a Miller blade and a Macintosh blade.

4. The laryngoscope simulator for training events of claim 1 wherein the microprocessor provides on-board recording capable of capturing video and audio.

5. The laryngoscope simulator for training events of claim 4 wherein the microprocessor includes a transmitter configured for selectively transmitting data from the laryngoscope.

6. The laryngoscope simulator for training events of claim 1 wherein the light source has lighting intensity adjustability that is adjustable by the operator.

7. The laryngoscope simulator for training events of claim 1 wherein the wherein the first blade portion is formed integral with the first handle portion as a molded component and the second blade portion is formed integral with the second handle portion as a molded component.

8. The laryngoscope simulator for training events of claim 5 wherein the event flagging further comprises remote event flagging.

9. A laryngoscope simulator for training events comprising:

a first handle portion;

a second handle portion coupled to the first handle portion, together defining a handle internal cavity, wherein the first handle and the second handle portions combine to form a handle assembly at a proximal end of the laryngoscope;

a first blade portion, wherein the first blade portion is formed integral with the first handle portion;

a second blade portion coupled to the first blade portion, together defining a blade internal cavity in at least a portion thereof, wherein the first blade portion and the second blade portion combine to form a conventional blade assembly at a distal end of the laryngoscope, wherein the second blade portion is formed integral with the second handle portion;

an integrated camera and light source within the internal cavity of the blade assembly for illuminating at least a portion of the blade assembly and for obtaining images of the operation of the laryngoscope;

a microprocessor coupled to the camera, said microprocessor mounted within one of the handle internal cavity and the blade internal cavity, wherein the microprocessor can record images from the camera and further receive and store event data, the event data comprising simulator data, external audio inputs, and external video inputs, wherein the microprocessor includes a transmitter configured for selectively transmitting data from the laryngoscope; and a keypad to provide on-board event flagging via the keypad of the recorded data recorded by the microprocessor.

10. The laryngoscope simulator for training events of claim 9 further comprising a transceiver to send and receive event flags remotely.

11. The laryngoscope simulator for training events of claim 10 wherein the blade assembly is one of a Miller blade and a Macintosh blade.

12. The laryngoscope simulator for training events of claim 9 wherein the microprocessor provides on-board recording capable of capturing video and audio.

13. The laryngoscope simulator for training events of claim 12 wherein the blade assembly is one of a Miller blade and a Macintosh blade.

14. The laryngoscope simulator for training events of claim 9 wherein the light source has lighting intensity adjustability that is adjustable by the operator.

15. The laryngoscope simulator for training events of claim 9 wherein the wherein the first blade portion is formed integral with the first handle portion as a molded component and the second blade portion is formed integral with the second handle portion as a molded component.

16. The laryngoscope simulator for training events of claim 9, wherein the event flagging further comprises remote event flagging.

* * * * *

UNITED STATES PATENT AND TRADEMARK OFFICE
CERTIFICATE OF CORRECTION

PATENT NO. : 9,622,651 B2  
APPLICATION NO. : 13/750156  
DATED : April 18, 2017  
INVENTOR(S) : Charles G. Miller et al.

Page 1 of 1

It is certified that error appears in the above-identified patent and that said Letters Patent is hereby corrected as shown below:

On the Title Page

Item (75) Inventors:  
Change "Clifford P Olmstead" to --Clifford D. Olmstead--

Signed and Sealed this  
Thirty-first Day of October, 2017

Joseph Matal  
*Performing the Functions and Duties of the*  
*Under Secretary of Commerce for Intellectual Property and*  
*Director of the United States Patent and Trademark Office*